United States Patent [19]

Harris et al.

[11] Patent Number: 5,769,804
[45] Date of Patent: Jun. 23, 1998

[54] CARPAL TUNNEL SYNDROME WRIST BRACE

[75] Inventors: Alvin R. Harris, Hackensack, N.J.; Christopher L. Vaughan, Claremont, South Africa

[73] Assignee: Becton Dickinson and Company, Franklin Lakes, N.J.

[21] Appl. No.: 686,885

[22] Filed: Jul. 26, 1996

[51] Int. Cl.$^6$ .................................................. A61F 5/00
[52] U.S. Cl. ................................ 602/21; 602/20; 602/64
[58] Field of Search ............................... 602/5, 20, 21, 602/64; 128/877, 878, 59–63; 2/161, 17, 162

[56] References Cited

U.S. PATENT DOCUMENTS

| | | | |
|---|---|---|---|
| 2,206,404 | 7/1940 | Jones | 602/21 |
| 4,382,439 | 5/1983 | Shen | 602/22 |
| 4,765,319 | 8/1988 | Finnieston et al. | 602/21 |
| 4,869,267 | 9/1989 | Grim et al. | 602/65 X |
| 5,205,812 | 4/1993 | Wasserman | 602/21 X |
| 5,409,451 | 4/1995 | Daneman | 602/21 |
| 5,513,657 | 5/1996 | Nelson | 602/20 |
| 5,577,516 | 11/1996 | Schaeffer | 128/887 |

*Primary Examiner*—Richard J. Apley
*Assistant Examiner*—Kim M. Lee
*Attorney, Agent, or Firm*—Alan W. Fiedler

[57] ABSTRACT

A carpal tunnel syndrome wrist brace including a shell having a first and second edge lined with a plurality of eyelets and both edges being connected together by a tongue stitched therebetween. The shell includes a thumb hole for receiving a thumb and is shaped to fit a patient's wrist such that the patient can insert the hand and wrist into the proximal end of the shell and extend four fingers through the distal end of the shell with the thumb through the thumb hole. The shell is then secured to the patient's wrist to activate immobilization of the wrist using a pair of hook and loop fasteners and a plurality of laces.

5 Claims, 7 Drawing Sheets

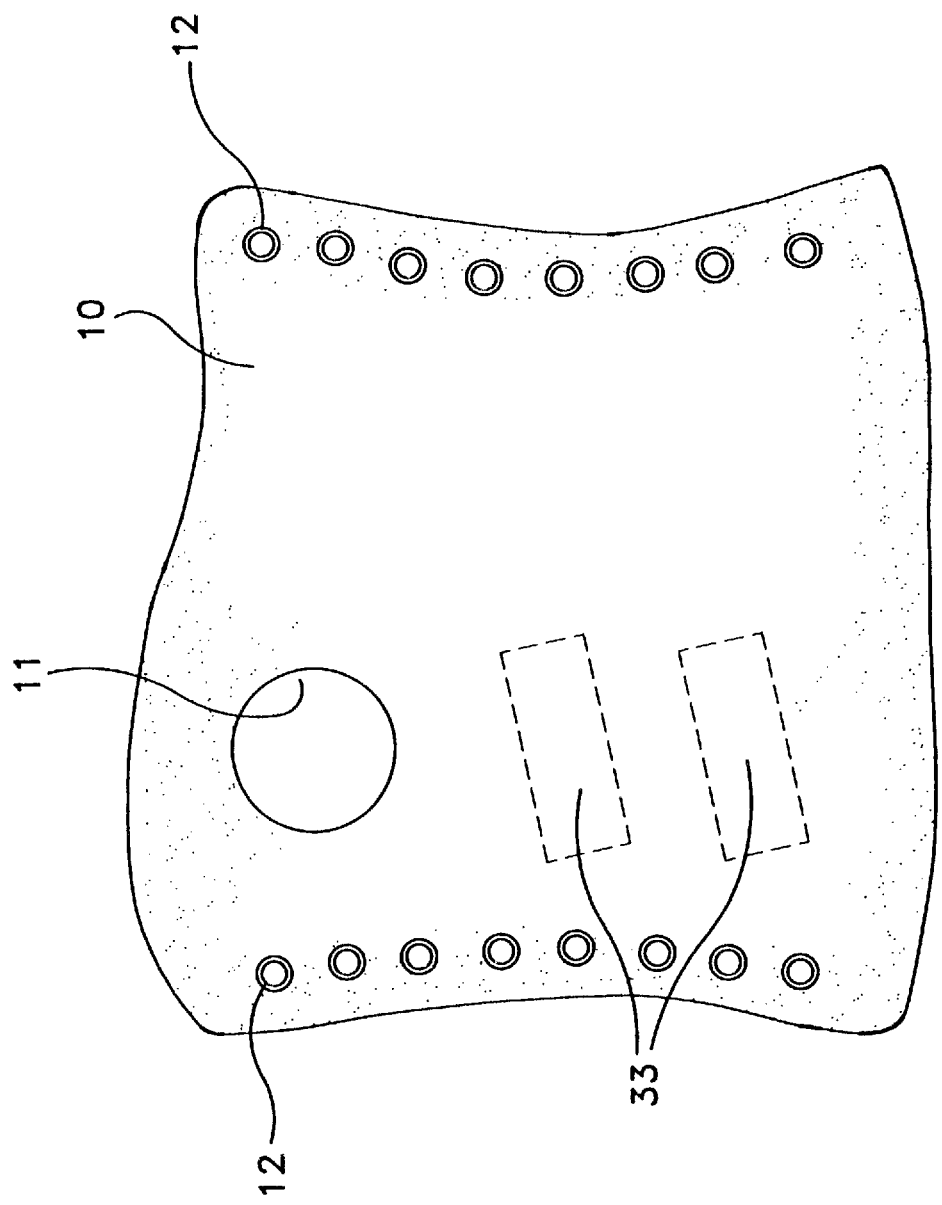

5,769,804

CARPAL TUNNEL SYNDROME WRIST BRACE

BACKGROUND OF THE INVENTION

1. Field of the Invention

The present invention relates to a carpal tunnel syndrome wrist brace and, more particularly, relates to a wrist brace for relieving the symptoms and slowing the progression of Carpal Tunnel Syndrome ("CTS").

2. Background Description

CTS is a condition that arises from pressure on the median nerve in the wrist. The median nerve enters the hand by passing through the "carpal tunnel" formed by the carpal bones and transverse carpal ligament in the wrist. When the median nerve is pinched it causes painful throbbing, tingling and numbness in the hand, wrist and forearm. In addition, CTS many times has symptoms including swollen hands and wrists. These symptoms often occur when the person is sleeping and may cause the person to wake up, but these symptoms can also happen during the day. CTS can affect all or any combination of a person's fingers and can cause the hand to become so weak that the person cannot hold on to objects as firmly as they could before.

CTS can be caused by many things, but is usually caused by continuously repeating the same motion with the hand and wrist. In fact, CTS is sometimes referred to as a Repetitive Motion Injury ("RMI"). Types of activities that can cause CTS symptoms include extended periods of writing, typing, holding a steering wheel, using power tools, craft work, and sports such as cycling, weightlifting and rowing. Other conditions can also affect CTS, including arthritis, diabetes, alcoholism, thyroid disease, wrist injuries, pregnancy and menopause. CTS affects an estimated 200,000 people a year. In fact, as many as 10% of all adults may experience CTS symptoms at one time or another.

A number of treatments have been proposed and used to relieve the symptoms of CTS including surgery, steroid injections into the carpal tunnel, diuretics, and splints. Of course, more conservative treatment is desired but depends on the cause of nerve compression. If symptoms are provoked by particular activities, modification of hand use during these activities is often prescribed. These modifications may include eliminating the activity, decreasing its duration, or interrupting it with periodic rest periods. A variety of medications have been used including hormones and many times braces, with or without splints, are used as both a preventive measure or as therapy for CTS. The problem with using splints, braces or other support equipment is that if they are used inappropriately, or if they change the way in which a worker performs a task, these devices can cause a different type of physical problem.

In addition to the above, CTS braces currently on the market provide immobilization of the wrist using a rigid support member consisting of a variety of shapes and materials, i.e., thermoformable plastics or metal. Such braces provide varying degrees of immobilization of the wrist: however, they do not provide control over flexion-extension in ulnar deviation.

SUMMARY OF THE INVENTION

The present invention overcomes the problems identified in the background material by providing a carpal tunnel syndrome wrist brace that relieves the symptoms and slows the progression of carpal tunnel syndrome.

A preferred embodiment of a carpal tunnel syndrome wrist brace according to the present invention includes a preformed shell shaped to fit the patient's wrist with a thumb hole through the shell for receiving the patient's thumb. An elastic tongue extends across the shell so that the shell fits snugly on the patient's wrist before being fully latched using a multi-strand lace extending over the elastic tongue. The multistrand lace is latched in place using a pair of self adhering hook and loop, i.e., Velcro™, fasteners.

These and other aspects, features and advantages of the present invention will become apparent from the following detailed description taken in conjunction with the accompanying drawings.

DESCRIPTION OF THE DRAWINGS

FIG. 7 is a top plan view of the shell portion of the carpal tunnel syndrome wrist brace shown in FIG. 1, unfolded prior to forming and assembly.

DETAILED DESCRIPTION

Figure 1:
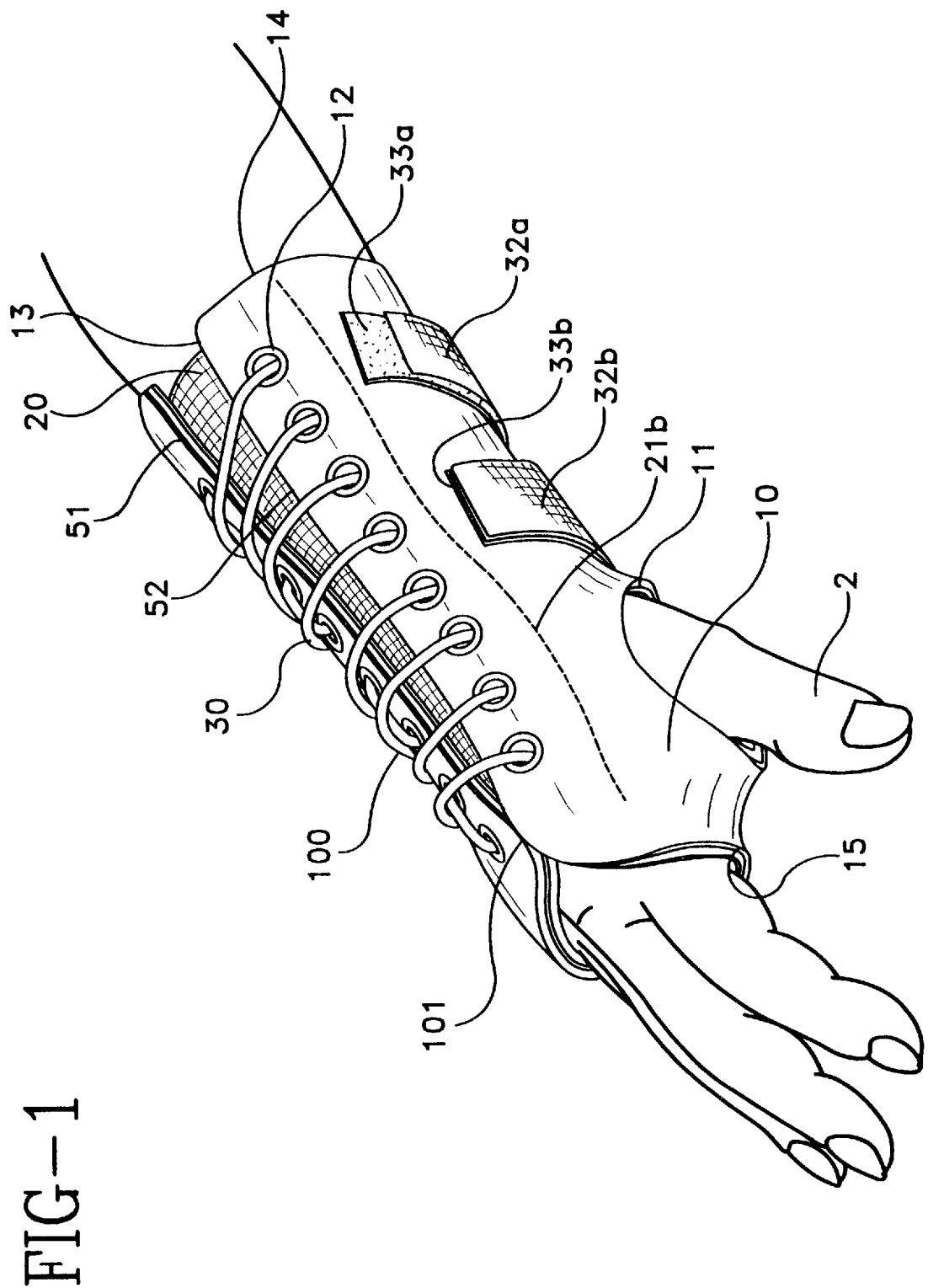
FIG. 1 is a perspective view of a carpal tunnel syndrome wrist brace according to the present invention during use on a patients wrist.

FIG. 1 is a perspective view of a carpal tunnel syndrome ("CTS") wrist brace 100 according to the present invention. FIG. 1 shows wrist brace 100 during use in a latched position on a patient's wrist 1.

Figure 2:
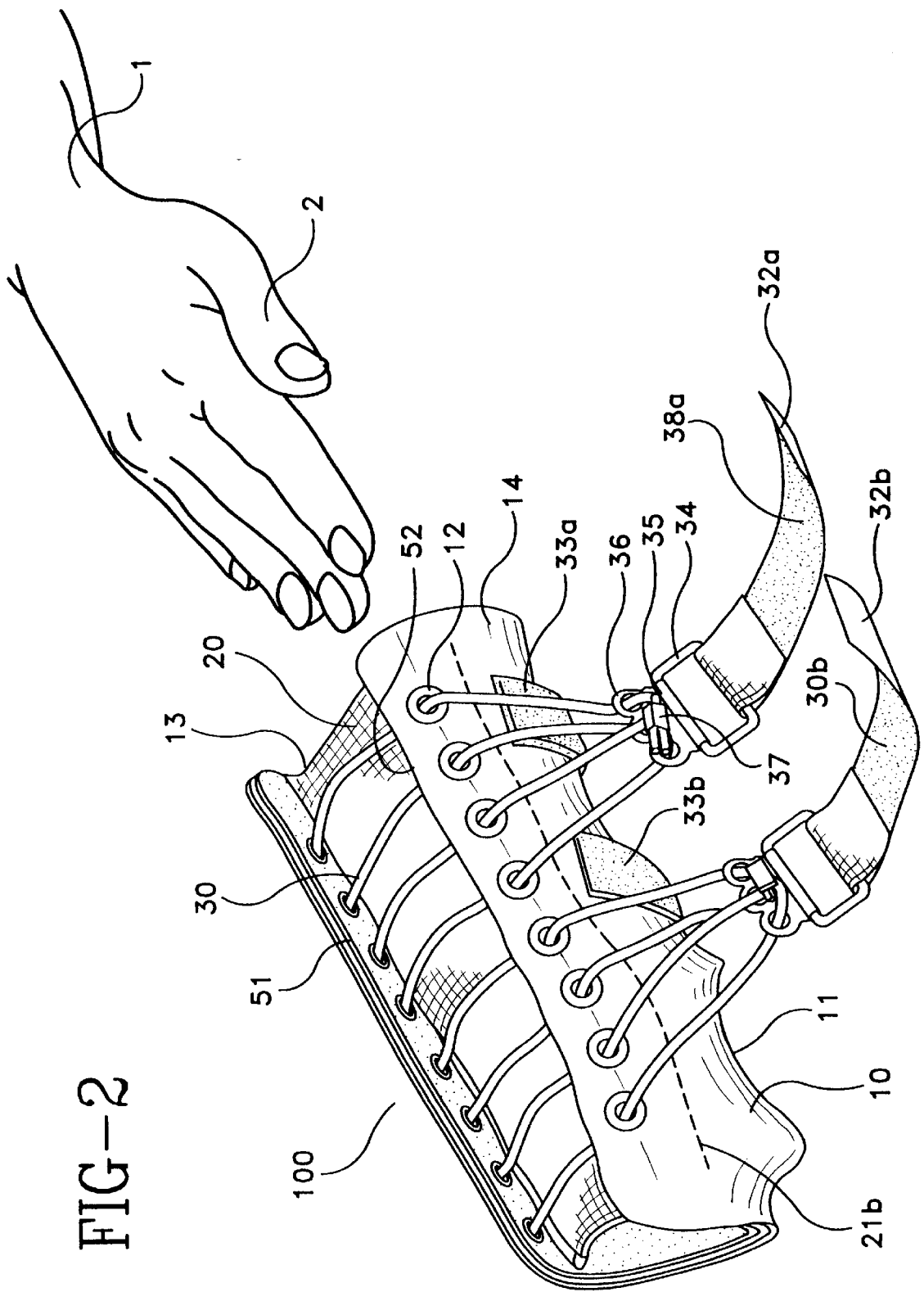
FIG. 2 is a perspective view of the carpal tunnel syndrome wrist brace shown in FIG. 1, in an unlatched position with the patient's wrist removed from the brace.

As shown in FIGS. 1 and 2, wrist brace 100 includes a shell 10 that is preformed to fit the patient's wrist 1. Shell 10 includes a thumb hole 11 through which the patient inserts a thumb 2 when placing brace 100 on wrist 1 as wrist 1 is inserted into proximal end 14 of shell 10. Shell 10 also includes an opening 13 formed by a first edge 51 and a second edge 52 on a top surface 101 that is attached together to close opening 13 using an elastic tongue 20. Elastic tongue 20 is stitched to both edges 51 and 52 of shell 10 using stitching 21a(FIG. 3) and 21b, respectively. Tongue 20 is made of an elastic material, i.e., bandage material, to allow shell 10 to be stretched open and accommodate wrists of various sizes. Elastic tongue 20 permits edges 51 and 52 on shell 10 to be opened sufficiently for a patient to insert their hand and wrist into proximal end 14 and through to distal end 15, with the patient's thumb 2 being inserted into thumb hole 11. During this process, wrist brace 100 is in the arrangement shown in FIG. 2.

FIG. 2 more clearly shows a pair of straps 32a and 32b, which are used to latch wrist brace 100 on the patient's wrist. As shown in FIG. 2, each strap 32a and 32b includes a hook/loop fastener 38a and 38b, respectively, a buckle 34, a flange 35 and a lace guide attachment 36. Fastener 38a/38b is attached by stitching to buckle 34, buckle 34 is attached to flange 35, and lace attachment 36 is attached to flange 35. Lace guide attachment 36 includes three holes 361, 362 and 363 that receive a number of strands 301, 302, 303 and 304 of non-elastic lace 30 with both ends of strands 301 and 304 on lace 30 being crimped, knotted or otherwise fastened by a fastener 37. When wrist brace 100 is in the unlatched position shown in FIG. 2, the proximal end 14 of brace 100 can be easily opened to receive the patient's hand.

Figure 3:
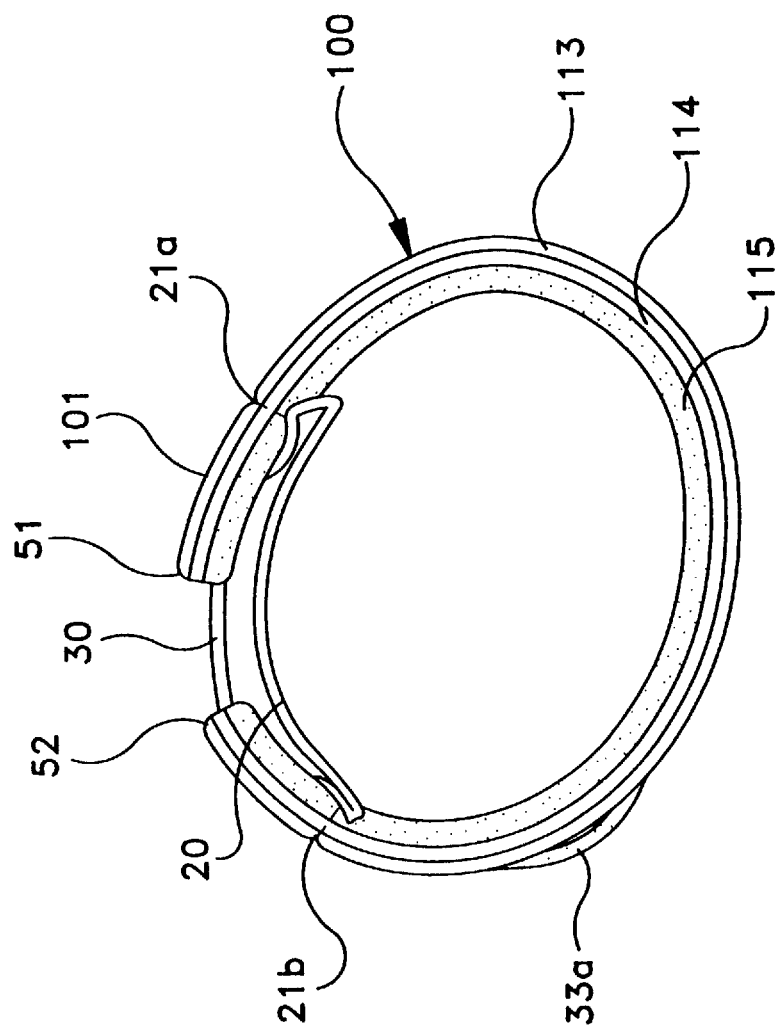
FIG. 3 is a proximal end view of the carpal tunnel syndrome wrist brace shown in FIG. 1.

FIG. 3 is a proximal end view of wrist brace 100 shown in FIG. 1 in the latched position that shows a three layer laminated material forming shell 10. The three layer laminated material includes a thermoformable plastic material outer layer 113, a terry cloth inner layer 115 and a middle adhesive binding layer 114. FIG. 3 also shows stitching 21a and 21b that attaches tongue 20 across opening shell 10.

The overall brace 100 has a Durometer hardness of 68 (Shore A), preferably in the range 61.2–74.8; a density of 12 lb/ft$^3$, preferably in the range 9.6–14.4; a tensile strength of 240 PSI, preferably in the range 192–288; a compressive strength of 50 PSI, preferably in the range 40–60; and an overall thickness of 0.235". The plastic material outer layer 113 preferably has a thickness of 0.125", the terry cloth layer 115 is made of 50% cotton and 50% polyester, and the adhesive binding layer 114 is 1/8" 2E Volara White Polyethylene foam.

Figure 4:
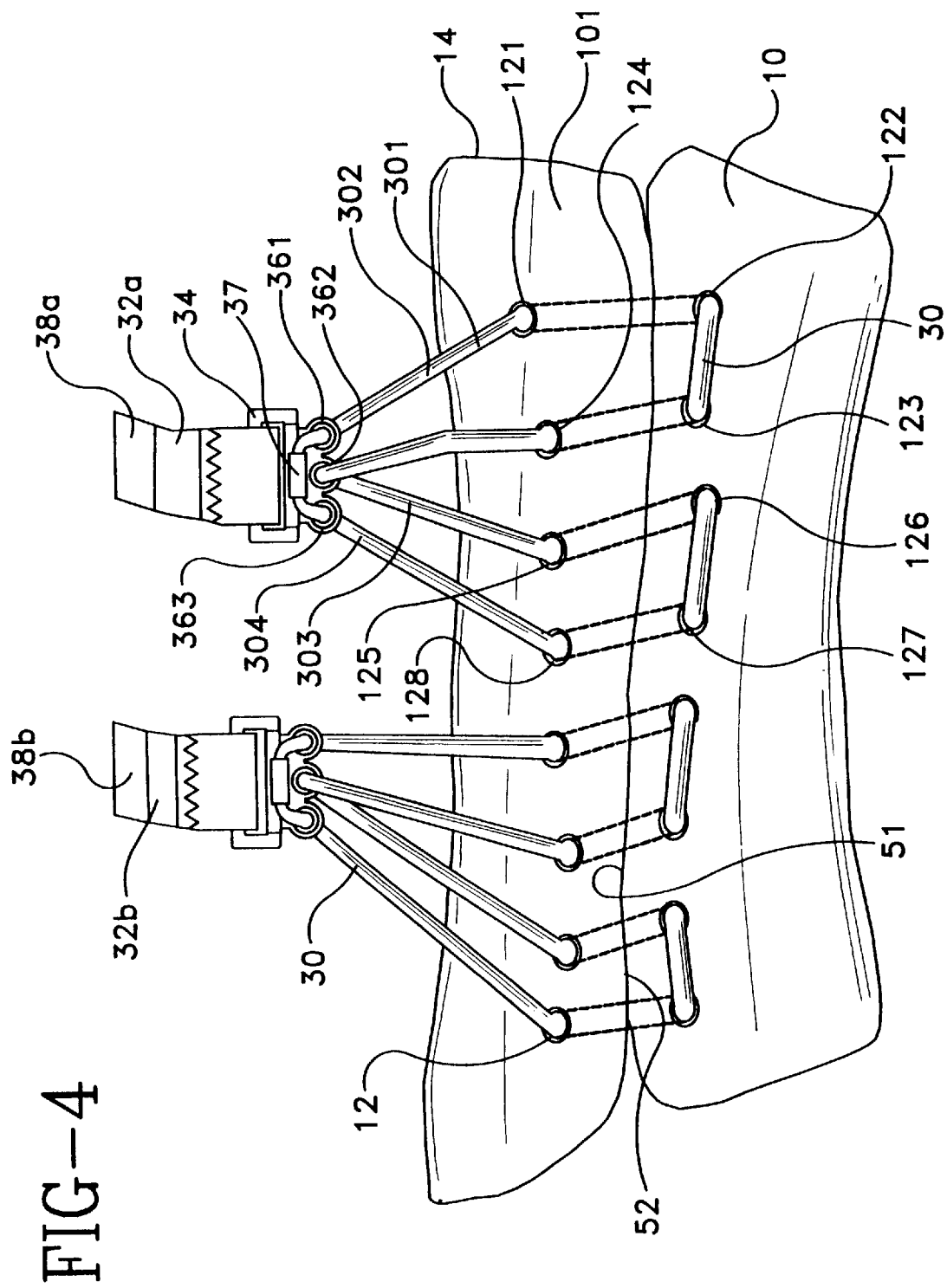
FIG. 4 is a top plan view of the carpal tunnel syndrome wrist brace shown in FIG. 2, with the brace in the unlatched position.

FIG. 4 is a top plan view of top surface 101 of wrist brace 100 shown in FIG. 2, with brace 100 in the unlatched position. In this position, straps 32a and 32b have been pulled to draw first edge 51 and second edge 52 together but are still not latched to their respective hook/loop fasteners 33a and 33b (FIG. 2). Straps 32a and 32b are preferably non-elastic. As shown in FIG. 4, each lace 30 starts at a first opening 361 on lace attachment 36 goes through an eyelet 121 on second edge 52 of shell 10, through another eyelet 122 on first edge 51 of shell 10, through another eyelet 123 on first edge 51 of shell 10, then back to another eyelet 124 on second edge 52, and then back to a central opening 362 on lace attachment 36. From central opening 362 lace 30 goes through an eyelet 125 at second edge 52, an eyelet 126 on first edge 51, another eyelet 127 on first edge 51, back to an eyelet 128 at second edge 52 and finally to a final opening 363 on lace attachment 36 where it is attached to the other end of lace 30 by attachment means 37. The same structure is used for strap 32b.

Figure 5:
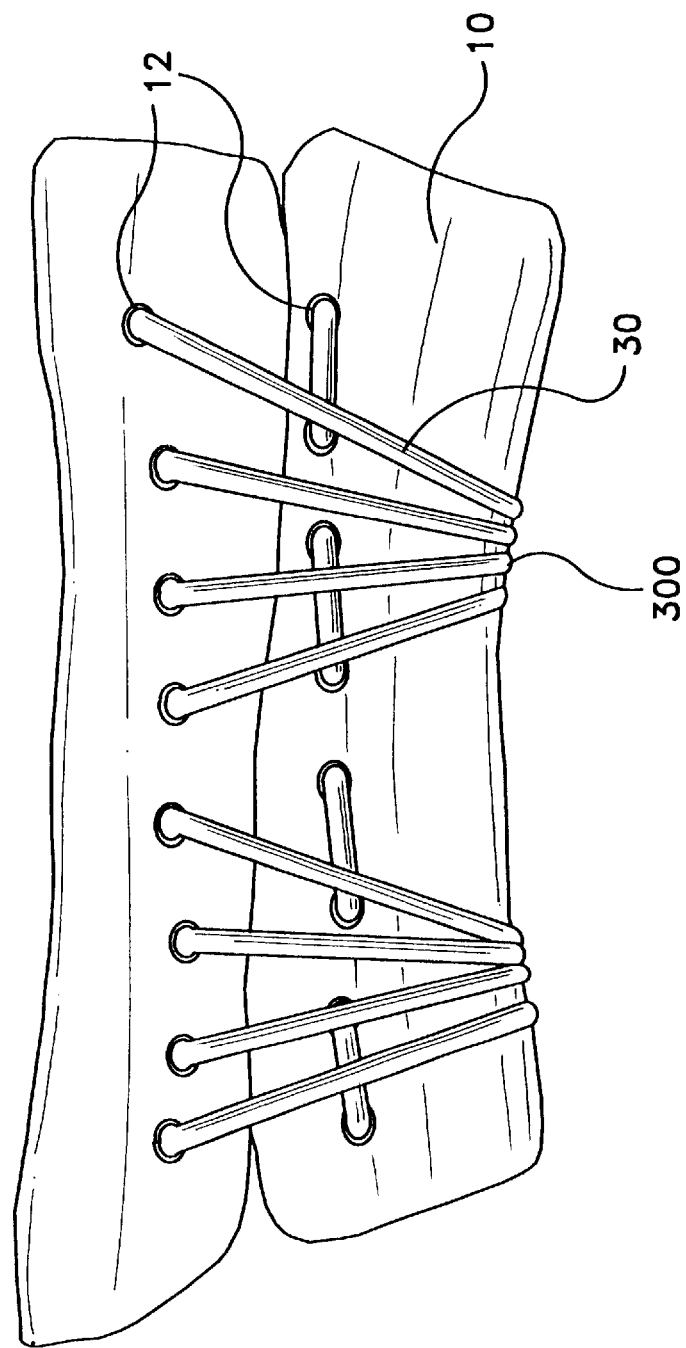
FIG. 5 is a top plan view of the carpal tunnel syndrome wrist brace shown in FIG. 1, with the brace in a latched position.
Figure 6:
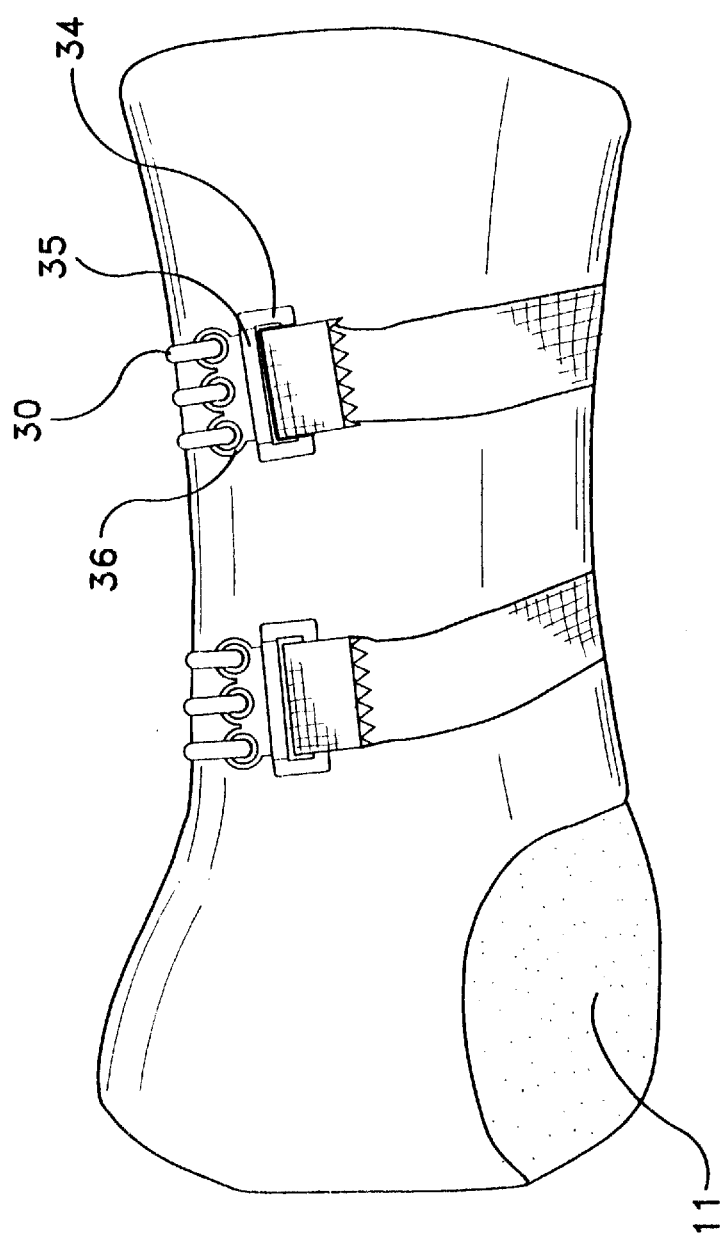
FIG. 6 is a bottom plan view of the carpal tunnel syndrome wrist brace shown in FIG. 5.

FIG. 5 is a top plan view of top surface 101 of wrist brace 100, shown in FIG. 1, with wrist brace 100 in the latched position. FIG. 5 shows strands 301, 302, 303 and 304 of lace 30 extending from second edge 52 of shell 10 over first edge 51 to converge at an apex 300 near hook/loop fasteners 33a and 33b (FIG. 1) on shell 10. This structure facilitates the closure of brace 100 to provide even distribution of all forces to immobilize wrist 1 as brace 100 is latched. FIG. 6 is a bottom plan view of wrist brace 100, shown in FIG. 5, with wrist brace 100 in the latched position. FIG. 6 clearly shows thumb hole 11 and how hook and loop fasteners 33 and 38 are attached at the bottom of shell 10.

Finally, FIG. 7 is a top plan view of shell 10 of wrist brace 100 unfolded after it has been die cut but prior to being preformed and assembled. FIG. 7 clearly shows the shape and location of thumb hole 11 and the plurality of eyelets 12 extending down first edge 51 and second edge 52 of shell 10. In addition, FIG. 7 shows the location of hook and loop fasteners 33a and 33b attached to shell 10.

The above-described brace can be manufactured using many materials and methods. However, the preferred materials and method include using a thermoformable plastic material layer 113 laminated to a terry cloth layer 115 using adhesive binding layer 114. Shell 10 is die cut using a Gerber machine or equivalent from 1/8" XPE thermoformable plastic material laminated with terry cloth layer 115 and shell 10 is then preformed. Shell 10 is designed and preformed to comfortably fit the wrist while immobilizing it for wrist movements (extensions, flexion, radial and ulnar deviation). A brace pattern is oriented on shell 10 in such a manner that the shell's width is in the bend direction when forming shell 10. The shell material is also isotropic and shrinks in its length direction on heating while its width remains constant. However, of course, these manufacturing techniques and materials are merely exemplary: various other manufacturing methods and materials could also be used. For example, buckle 34 and lace guide attachment 36 can be made as one molded piece thus eliminating the need for flange 35 and can be made of plastic or metal.

In the foregoing discussion, it is to be understood that the above-described embodiment of the present invention is simply illustrative of various features that can be used in a carpal tunnel syndrome wrist brace. Other suitable variations, modifications and combinations of these features could be made to or used in this embodiment and still remain within the scope of the present invention.

What is claimed is:

1. A carpal tunnel syndrome wrist brace comprising:
    a rigid shell formed to immobilize a wrist, said rigid shell comprising a proximal end, a distal end, a thumb hole located at said distal end, and an open top surface having a first edge and a second edge;
    a plurality of eyelets located on said first and second edges of said open top surface of said rigid shell; and
    means for securing said shell to the wrist and activating immobilization of the wrist comprising a pair of non-elastic straps, wherein each of said pair of non-elastic straps includes:
        a lace guide attachment; and
        a lace having a plurality of strands that are received by said plurality of eyelets on said shell and converge to an apex at said lace guide attachment.

2. A carpal tunnel syndrome wrist brace according to claim 1, wherein said rigid shell further comprises an elastic tongue attached between said first and second edge to allow said rigid shell to be stretched open and receive the wrist in the proximal end.

3. A carpal tunnel syndrome wrist brace according to claim 1, wherein said rigid shell is made of a laminated material.

4. A carpal tunnel syndrome wrist brace according to claim 3, wherein said laminated material comprises a thermoformable plastic material laminated to a terry cloth material.

5. A carpal tunnel syndrome wrist brace according to claim 1, wherein each of said pair of straps comprises a hook and loop fastener that latches to a corresponding hook and loop fastener on said rigid shell.

* * * * *